United States Patent
Attolini et al.

(10) Patent No.: US 8,070,724 B2
(45) Date of Patent: Dec. 6, 2011

(54) APPARATUS FOR EXTRACTING MILK FROM A BREAST AND RELATED PUMP UNIT

(75) Inventors: Emilio Attolini, Parma (IT); Andrea Bianchi, Roccabianca (IT)

(73) Assignee: Medel Group S.p.A., Torrile (IT)

( * ) Notice: Subject to any disclaimer, the term of this patent is extended or adjusted under 35 U.S.C. 154(b) by 0 days.

(21) Appl. No.: 12/742,883

(22) PCT Filed: Mar. 7, 2008

(86) PCT No.: PCT/IB2008/050837
§ 371 (c)(1),
(2), (4) Date: May 13, 2010

(87) PCT Pub. No.: WO2009/063338
PCT Pub. Date: May 22, 2009

(65) Prior Publication Data
US 2010/0262072 A1    Oct. 14, 2010

(30) Foreign Application Priority Data
Nov. 14, 2007 (IT) .............................. PR2007A0089

(51) Int. Cl.
*A61M 1/00* (2006.01)

(52) U.S. Cl. ...................................................... 604/119

(58) Field of Classification Search ................. 604/74, 604/119
See application file for complete search history.

(56) References Cited

U.S. PATENT DOCUMENTS

| | | | | |
|---|---|---|---|---|
| 5,009,638 | A * | 4/1991 | Riedweg et al. | 604/74 |
| 6,461,324 | B1 * | 10/2002 | Schlensog | 604/74 |
| 6,749,582 | B2 * | 6/2004 | Britto et al. | 604/74 |
| 2003/0204164 | A1 * | 10/2003 | Britto et al. | 604/74 |
| 2004/0249340 | A1 * | 12/2004 | Britto et al. | 604/74 |
| 2005/0015045 | A1 | 1/2005 | Tashiro et al. | |
| 2005/0159701 | A1 | 7/2005 | Conaway | |
| 2005/0256449 | A1 * | 11/2005 | Tashiro | 604/74 |
| 2006/0111664 | A1 * | 5/2006 | Samson et al. | 604/74 |
| 2007/0078383 | A1 * | 4/2007 | Tashiro et al. | 604/74 |
| 2008/0281262 | A1 * | 11/2008 | Nuesch | 604/74 |
| 2010/0174232 | A1 * | 7/2010 | Wortley et al. | 604/74 |

FOREIGN PATENT DOCUMENTS
EP    1 532 992 A1    5/2005

* cited by examiner

*Primary Examiner* — Jackie Ho
*Assistant Examiner* — Diva Ranade
(74) *Attorney, Agent, or Firm* — Pearne & Gordon LLP (57) ABSTRACT

An apparatus (1) for extracting milk from a breast, comprising means (2,3) for receiving at least a portion of a breast and its nipple; a container (5) for collecting the milk operatively connected to said means (2,3) for receiving at least partially a breast and its nipple; a pump unit (100) operatively connected to said means (2,3) for receiving at least partially a breast and its nipple, said pump unit (100) being operated manually to generate at least an aspiration able to cause a suction on the breast by imposing a predetermined degree of vacuum within said means for receiving the breast and the nipple. The manually operated pump unit (100) comprises means for regulating the degree of vacuum that is generated. Pump unit (100) operated manually and connectable to a kit for collecting milk from a breast.

20 Claims, 6 Drawing Sheets

APPARATUS FOR EXTRACTING MILK FROM A BREAST AND RELATED PUMP UNIT

TECHNICAL FIELD AND BACKGROUND ART

The present invention relates to an apparatus for extracting milk from a breast, of the type described in the preamble to claim 1.

The present invention also relates to a pump unit for an apparatus for extracting milk from a breast, of the type described in the preamble to claim 13.

As is well known, apparatuses for extracting human breast, so-called breast pumps, generally comprise a kit for collecting the milk connected to an aspirating pump.

Typically, the collection kit comprises a rigid cup provided with a flexible inner coating and able to receive a breast, a container for collecting the milk connected to the cup and a second end connected to the aspirating pump.

The vacuum generated by the pump is of the pulsated type and it determines a suction on the breast within the cup, extracting the milk which thus flows within the coating and then slides into the collecting container.

In accordance with a first prior art, there are breast pumps provided with an electromechanical aspirating pump.

An important drawback of the first prior art is that the presence of an electromechanical pump does not allow to use the breast pump in the absence of a source of electrical energy, be it the electrical mains or a battery.

To overcome this drawback, breast pumps provided with a manually operated pump have been developed.

In accordance with a second prior art, there are breast pumps that comprise s kit for collecting the milk connected to a manually operated pump unit.

Generally, the kit for collecting the milk comprises a rigid cup, in whose interior is inserted a flexible coating, shaped in substantially complementary fashion to the inner surface of the cup.

The cup and the coating are able to receive at least one portion of a breast and its nipple and they are connected to a container for collecting milk.

Generally, the pump unit comprises a piston slidably inserted in a cylinder communicating with an aspiration conduit connected to the flexible coating. The head of the piston, moving with alternating motion within the cylinder between two operating positions that define different volumes of the cylinder, produce a cyclic aspirating and thus generates a predetermined degree of pulsating vacuum degree within the flexible coating.

Some breast pumps, instead of a normal piston, use a membrane piston that comprises an elastic membrane connected to the lateral walls of the cylinder and fixed on the head of the piston.

Note that, both in the case of a membrane piston, and in the case of a traditional piston, the alternating motion of the piston is activated by mechanical means connected to a stem of the piston itself and included in the pump unit.

In particular, said mechanical means generally comprise a lever with its fulcrum on a support structure, said lever having a first end connected to the stem of the piston and a second end that can be gripped by a user, in such a way that to an alternating rotation of the lever around an axis passing through the fulcrum corresponds and alternating motion of the piston within the cylinder.

Depending on the dimensions of the lever and on the position of the fulcrum, the ratio between the stroke of the piston and the travel of the lever is pre-set and constant.

An important drawback of the breast pumps provided with a manually operated pump assembly and constructed in accordance with the second prior art is the impossibility of varying the degree of vacuum generated by the piston. Since the ratio between the stroke of the piston and the travel of the lever is precept, the degree of vacuum generated by the pump unit is also pre-set.

DISCLOSURE OF INVENTION

An object of the present invention is to solve the aforementioned drawbacks, making available an apparatus for extracting milk from a breast, provided with a manually operated pump unit which enables to adjust the degree of vacuum that is generated.

Another object of the present invention is to provide an apparatus for extracting milk from a breast that is reliable and simple to manufacture.

A further object of the present invention is to provide a pump unit for an apparatus for extracting milk from a breast that is manually operated and that enables to adjust the degree of vacuum that is generated.

Another object of the present invention is to propose a pump unit that is applicable on existing milk collection kits.

Said objects are fully achieved by the apparatus for extracting milk from a breast and from the pump unit of the present invention, which are characterised by the content of the appended claims.

BRIEF DESCRIPTION OF THE DRAWINGS

These and other objects shall become more readily apparent from the description that follows of a preferred embodiment, illustrated purely by way of non limiting example in the accompanying drawing tables, in which.

BEST MODE FOR CARRYING OUT THE INVENTION

Figure 1:
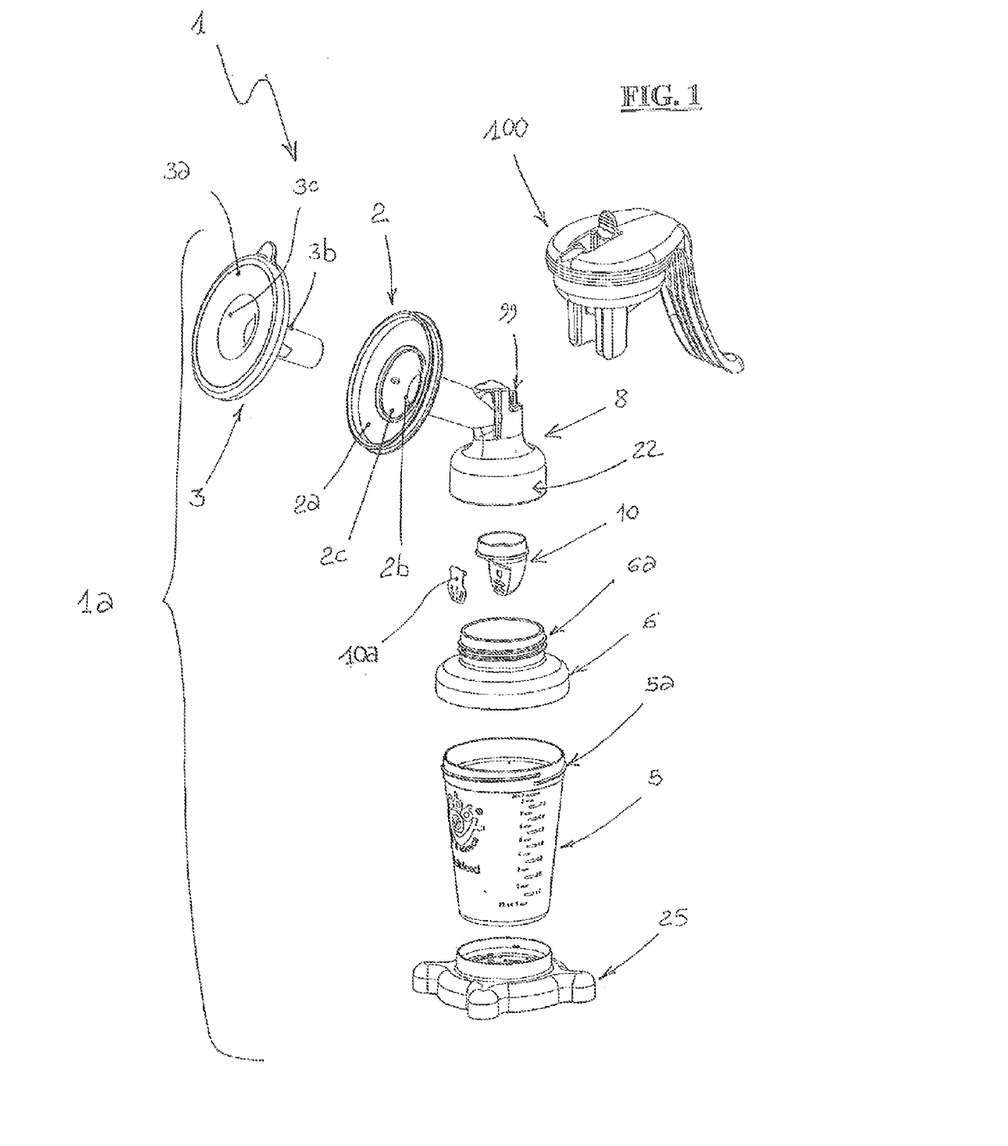
FIG. 1 shows an exploded view of an apparatus for extracting milk from a breast in accordance with the present invention, provided with a pump unit according to the invention.
Figure 2:
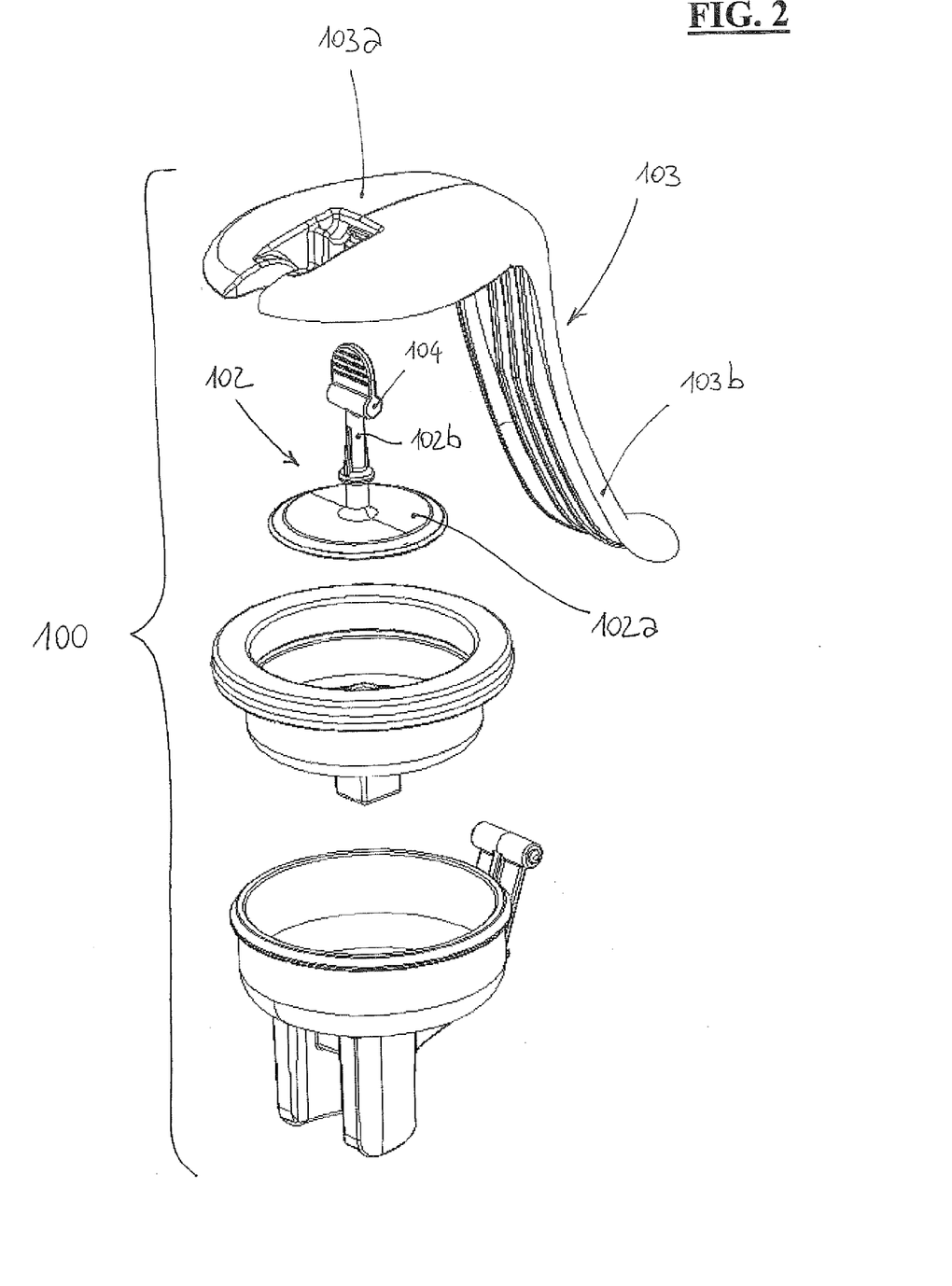
FIG. 2 shows an exploded view of the pump unit shown in FIG. 1.

With particular reference to FIG. 1, an apparatus for extracting milk from a breast is indicated in its entirely by the number 1.

The apparatus 1 comprises a milk collection kit 1*a* connected to a pump unit indicated in its entirety by the number 100.

Merely by way of example, an apparatus for extracting milk from a breast shall now be described in which the pump unit 100 can be physically separated by the milk collection kit.

It is readily apparent that the scope of protection of the present invention also includes an apparatus for extracting milk from a breast, in which the pump unit 100 is integrally connected to the apparatus itself or, alternatively, it is obtained in a single piece with the apparatus.

The kit 1a comprises a rigid case 2, preferably a cup having a funnel portion 2a, a choke 2b and a junction portion 2c interposed between said funnel portion and said choke.

A flexible tubular body 3 is inserted in the rigid case 2 and is able to receive at least a portion of a breast and a nipple thereof. Preferably, the flexible tubular body 3 is made of a polymeric or silicone material, typically rubber or neoprene. Preferably, the flexible tubular body 3 is shaped complementarily to the rigid case 2 and hence it presents a funnel portion 3a, a choke 3b and a junction portion 3c interposed between said nozzle portion and said choke.

The kit 1a comprises a container 5 for collecting the milk, operatively connected to the tubular body 3. In the illustrated example, the container 5 is preferably provided with a threaded portion 5a, whereon is screwed a flange 6 having a threaded expansion 6a able to engage in a corresponding counter-thread obtained in a base portion 22 of a header 8.

Preferably, the container 5 couples with a supporting stand 25.

Figure 3:
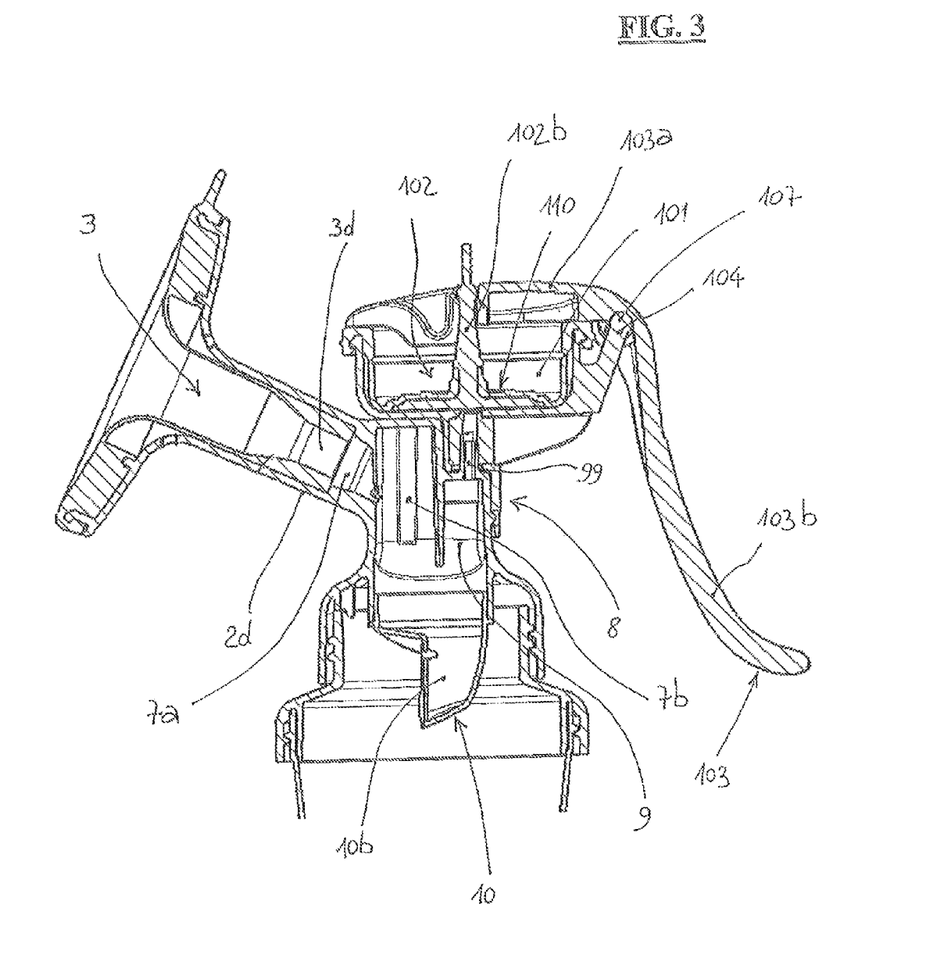
FIG. 3 shows a sectioned lateral view of the apparatus shown in FIG. 1.
Figure 4:
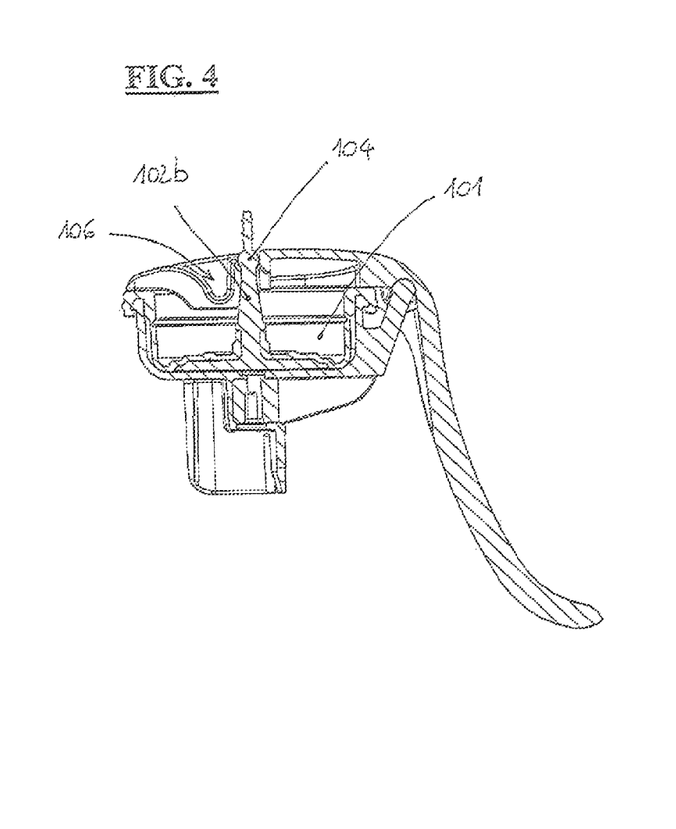
FIGS. 4 and 5 show two lateral sectioned views of the pump unit shown in FIG. 2 in a first operative configuration, but in two different operating positions.

With particular reference to FIG. 3, the tubular body 3 has a terminal portion 3d so shaped as to couple, in sealed fashion, to a first conduit 7a for the collection of the milk housed internally to a terminal portion 2d of the rigid case 2.

The terminal portion 2d of the rigid case 2 engages in the connector 8, within which is present a second conduit 7b for the collection of the milk which defines a continuation of said first collection conduit 7a.

Within the header 8 is also present an aspiration compartment 9 having an aspiration conduit 99 (shown also in FIG. 1) connectable to the pump unit 100. The aspiration unit 9 communicates with the first and the second milk collection conduit 7a, 7b, in such a way that a predetermined degree of vacuum is generated within the tubular body 3. In this way, a suction on the breast is determined within the tubular body 3, extracting the milk which thus flows within the tubular body and then slides into the collecting container 5.

With reference to FIGS. 1 and 3, a one-way valve 10 is preferably installed at the base of the header 8, at an outlet of said second collection conduit 7b. Said valve 10 is able to convey into the container 5 the milk coming from the tubular body 3 through the first and the second collection conduit 7a, 7b.

The one-way valve 10 comprises a shutter 10a (FIG. 1), preferably a tongue, movable between a position of opening and a position of closing a hole for the passage of the milk. In particular, the shutter moves by effect of the weight of the milk that is collected in an accumulation chamber 10b obtained within the valve itself.

The shutter 10a has edges able to bear on corresponding outer abutment surfaces of the accumulation chamber Mb, in such a way as to prevent the flow of milk from the collection container 5 to the header 8 and to allow, instead, solely the flow of milk from the header 8 to the container 5.

With particular reference to FIGS. 2 through 7, the pump unit 100 comprises a chamber 101 within which is housed a piston 102, having a head 102a and a stem 102b.

The chamber 101 is operatively connected and communicates with the aspiration conduit 99 of the header 8 and hence with the aspiration compartment 9.

Preferably, the piston 102 comprises an elastic membrane 110, fastened to portions 101a, 101b of the chamber 101 and integrally connected to the head 102a of the piston 102. Preferably, the membrane 110 entirely coats the head of the piston, with the exception of the connection region between the stem 102b and the head.

Typically, the membrane is made of a polymeric or silicone material.

A linkage 103 is pivotally engaged on a support structure 104 of the pump unit 100 and it has a first portion 103a removably connected to an abutment element 104 of the stem 102b, and a second portion 103b which can be gripped by a user, in such a way that to an alternating rotation of the linkage around an axis passing through the fulcrum 107 corresponds an alternating motion of the piston within the chamber.

Figure 8:
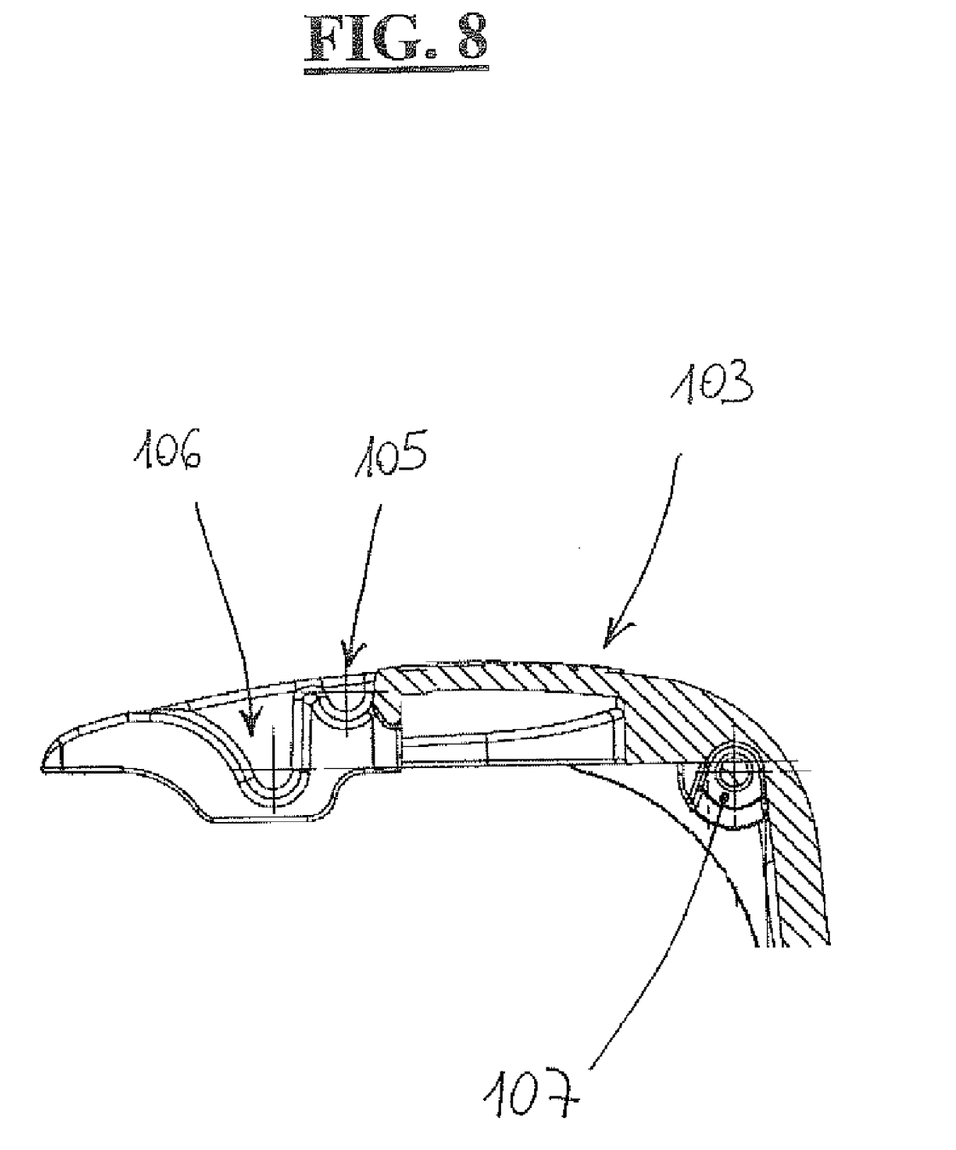
FIG. 8 shows a sectioned view of a constructive detail of the pump unit shown in FIG. 2.

With particular reference to FIG. 8, the linkage 103 has at least a first housing 105 and at least a second housing 106, each of which is able selectively to house said abutment element 104 of the stem 102b. Said housings are differently positioned and/or shaped in such a way as to vary the stroke of the piston within the chamber 101. In particular, when the abutment element 104 is positioned in the housing 105, the stroke of the piston will be the longest, whilst when the abutment element 104 is positioned in the housing 106, the stroke of the piston will be the shortest. The housings are positioned and/or shaped in such a way as to engage the abutment element 104 at different angular positions assumed by the linkage 103 during its rotation around the axis passing through the fulcrum 107.

In the preferred embodiment, the housings 105, 106 are defined by two grooved profiles obtained on the first portion 103a of the linkage 103 and having a different development, in such a way that the abutment element 104, when the linkage is completely rotated, reaches different heights with respect to the base of the camera 101. In particular, the grooved profiles are defined by recesses obtained on said first portion 103a of the linkage 103, so that the recess corresponding to a first one of said grooved profiles (housing 106) extends in said first portion of the linkage more in depth than the recess corresponding to a second one of said grooved profiles (housing 105).

Preferably, the housings 105, 106 are adjacent and they are positioned at different distances from the fulcrum 107 of the linkage. In particular, the distance of the first housing 105, corresponding to the maximum stroke of the piston from the fulcrum 107, is smaller than the distance of the second housing 106, corresponding to the shortest stroke of the piston.

In accordance with an embodiment variant, not shown, said housings may be obtained with grooved profiles having identical development, but positioned at different distances from the fulcrum of the linkage.

The operation of the invention is as follows.

With reference to FIG. 3, a user exerts a force on the linkage 103, which, being connected to the stem 102b of the piston 102, lifts the membrane and creates a vacuum inside the aspiration compartment 9. The displacement of the membrane 110 causes the formation of a volume 150, within which flows the air present in the aspiration compartment, determining a vacuum in the header 8 and hence in the tubular body 3. Said vacuum causes suction on the breast in the tubular body, extracting the milk.

Figure 5:
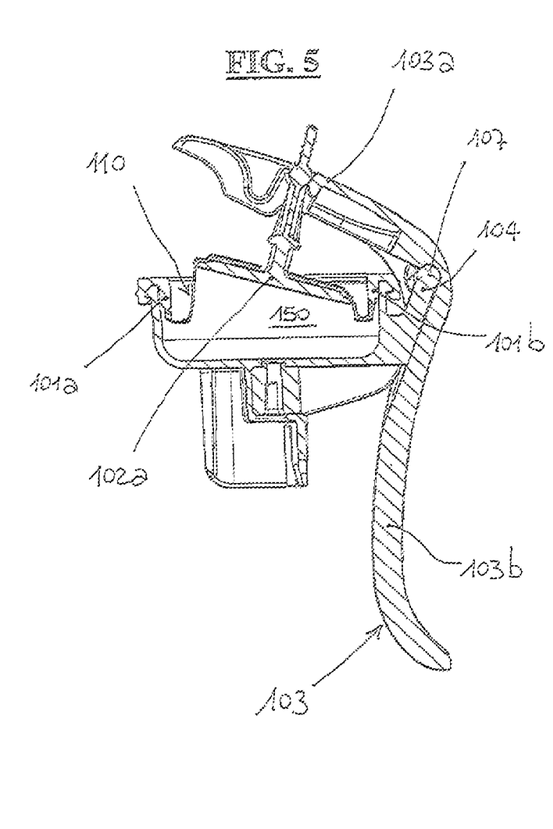

With reference to FIG. 5, when the abutment element 104 of the stem 102b of the piston is positioned in the first housing 105, the linkage 103 lifts the piston and hence the membrane through its entire stroke, thereby generating the maximum degree of vacuum, because the volume 150 defined within the chamber 101 by the displacement of the membrane is the largest.

Figure 6:
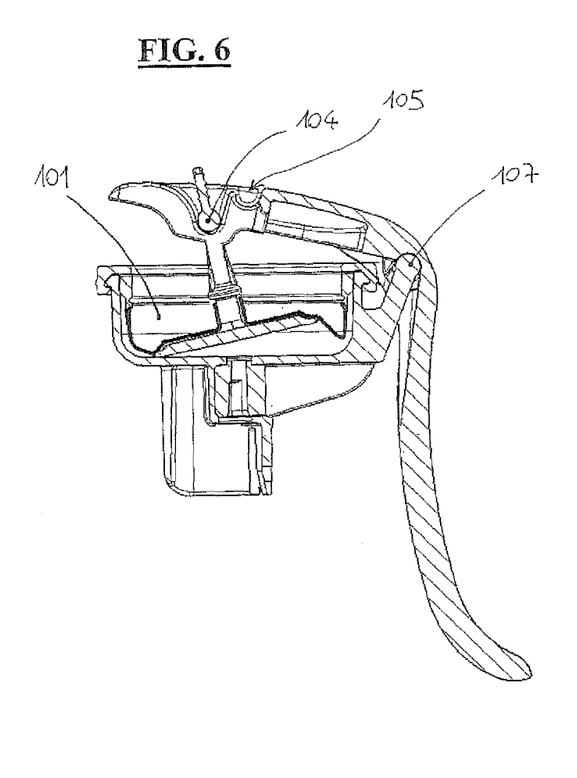
FIGS. 6 and 7 show two lateral sectioned views of the pump unit shown in FIG. 2 in a second operative configuration, but in two different operating positions.
Figure 7:
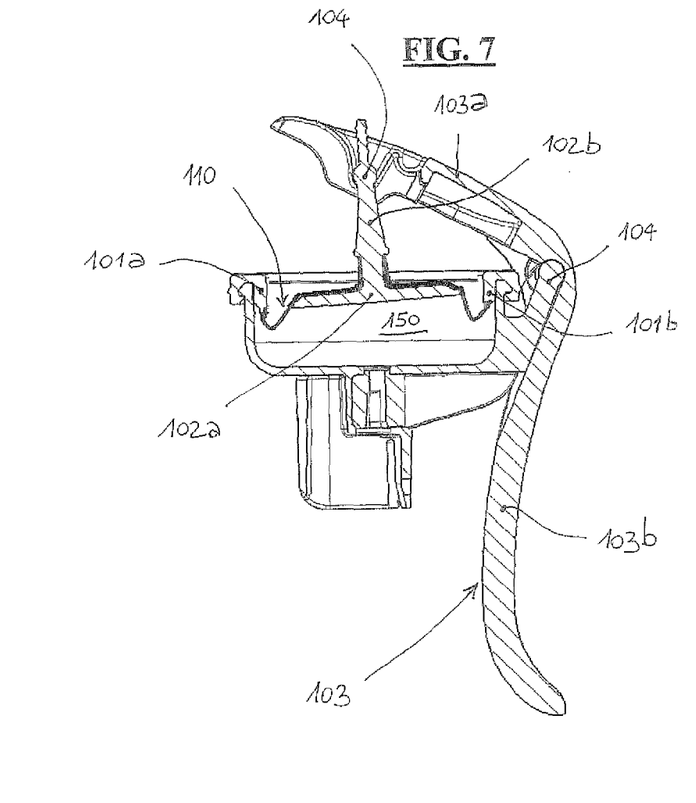

With reference to FIG. 6, when the abutment element 104 of the stem 102b of the piston is positioned in the second housing 106, the linkage 103 rotates idly around the fulcrum 107 for a first part of its travel, without lifting the membrane 110. With reference to FIG. 7, the linkage, in a second part of its travel equivalent to about half the total travel, starts to lift the membrane 110, generating a lower degree of vacuum than obtained with the stem of the piston positioned in said first housing 105. In this case, the degree of vacuum is minimum, because the volume 150 defined within the chamber 101 by the displacement of the membrane is the smallest.

The positioning of the abutment element 104 within the housings 105, 106 is accomplished by pulling the stem 102b of the piston, exploiting the elasticity of the membrane.

The repositioning of the linkage 103 is obtained exploiting the elasticity of the membrane and the pressure differential that is created between the ambient pressure acting on the exterior of the membrane and the vacuum generated within the chamber 101 by effect of the displacement of the membrane.

The invention achieves important advantages.

First of all, while an apparatus for extracting milk from a breast in accordance with the invention is able to operate also in the absence of electrical power, enables to operate an adjustment of the degree of vacuum generated and hence on the level of suction on the breast within the apparatus.

An additional advantage of the present invention is that a pump unit in accordance with the invention can also be applied on existing milk collection kits, with minimal structural modifications. It is sufficient to manufacture an adapter to interface the pump unit to an aspiration inlet present on the kit.

Advantageously, an apparatus for extracting milk from a breast and a pump unit in accordance with the invention are reliable and simple to build, because they do not need complicated valve systems.

The invention claimed is:

1. An apparatus (1) for extracting milk from a breast, comprising:
    means (2,3) for receiving at least a portion of a breast and its nipple;
    a container (5) for collecting the milk, operatively connected to said means for receiving at least partially a breast and its nipple;
    a pump unit (100) operatively connected to said means (2,3) for receiving at least partially a breast and its nipple, said pump unit (100) being operated manually to generate at least an aspiration able to cause a suction on the breast by imposing a predetermined degree of vacuum within said means for receiving the breast and the nipple, said manually operated pump unit (100) comprising means for regulating the degree of vacuum that is generated, wherein said pump unit comprises:
    a chamber (101) operatively communicating with said means (2,3) for receiving at least partially a breast and its nipple;
    a piston (102) housed internally to said chamber (101) and movable at least between a resting position and an operative position of aspiration;
    a linkage (103) pivotally engaged with its fulcrum on a support structure and having a first portion (103a) removably connected to a stem (102b) of the piston and a second portion (103b) which can be gripped by a user, so that to an alternating rotation of the linkage (103) around an axis passing through the fulcrum (107) corresponds an alternating motion of the piston (102) within the chamber (101),
    characterized in that said means for regulating the degree of vacuum are defined by a pair of housings (105,106) obtained on said first portion (103a) of the linkage (103) and able selectively to house an abutment element (104) integral with a stem (102b) of the piston (102), said housings being shaped and/or positioned in such a way as to engage said abutment element at different angular positions assumed by the linkage during its rotation around said axis passing through the fulcrum (107).

2. An apparatus as claimed in claim 1, wherein at least one of said housings (105,106) is defined by a grooved profile obtained on said first portion (103a) of the linkage (103).

3. An apparatus as claimed in claim 1, wherein each of said housings (105,106) is defined by a grooved profile obtained on said first portion (103a) of the linkage (103).

4. An apparatus as claimed in claim 3, wherein said grooved profiles are defined by recesses obtained on said first portion (103a) of the linkage (103), the recess corresponding to a first one of said grooved profiles extending more in depth in said first portion of the linkage than the recess corresponding to a second one of said grooved profiles.

5. An apparatus as claimed in claim 1, wherein said housings (105,106) are positioned at different distances from the fulcrum (107).

6. An apparatus as claimed in claim 1, wherein said pump unit comprises an elastic membrane (110) fastened to portions (101a,101b) of the chamber (101) and integrally connected to a head (102a) of said piston (102).

7. An apparatus as claimed in claim 6, wherein said elastic membrane (110) coats at least partially the head (102a) of the piston (102).

8. An apparatus as claimed in claim 6, wherein said elastic membrane (110) coats the head (102a) of the piston (102) entirely, excepting the region connecting the stem (102b) to the head.

9. An apparatus as claimed in claim 1, wherein said means for receiving at least a portion of a breast and its nipple comprise:
    a rigid case (2);
    a flexible tubular body (3) inserted in said rigid case (2) and able to receive at least a portion of a breast and of its nipple, said tubular body being operatively connected to said pump group (100) to cause a suction on the breast within the tubular body by means of a predetermined degree of vacuum.

10. An apparatus as claimed in claim 9, wherein said tubular body (3) is complementarily shaped relative to said rigid case (2).

11. Pump unit (100) operated manually and connectable to a kit for collecting milk from a breast, said pump unit generating at least an aspiration able to cause a suction on the breast by imposing a predetermined degree of vacuum, said pump unit comprising means for regulating the degree of vacuum that is generated, wherein said pump unit comprises:
    a chamber (101) operatively connectable and communicating with an aspiration conduit (99) of a milk collection kit;
    a piston (102) housed internally to said chamber (101) and movable at least between a resting position and an operative position of aspiration;
    a linkage (103) pivotally engaged with its fulcrum on a support structure and having a first portion (103a) removably connected to a stem (102b) of the piston and a second portion (103b) which can be gripped by a user, so that to an alternating rotation of the linkage around an axis passing through the fulcrum (107) corresponds an alternating motion of the piston within the chamber,
    characterized in that said means for regulating the degree of vacuum are defined by a pair of housings (105,106) obtained on said first portion (103a) of the linkage (103) and able selectively to house an abutment element (104) integral with a stem (102b) of the piston (102), said housings being shaped and/or positioned in such a way as to engage said abutment element at different angular positions assumed by the linkage (103) during its rotation around said axis passing through the fulcrum (107).

12. Pump unit as claimed in claim 11, wherein at least one of said housings (105,106) is defined by a grooved profile obtained on said first portion (103*a*) of the linkage (103).

13. Pump unit as claimed in claim 11, wherein each of said housings (105,106) is defined by a grooved profile obtained on said first portion (103*a*) of the linkage (103).

14. Pump unit as claimed in claim 13, wherein said grooved profiles are defined by recesses obtained on said first portion (103*a*) of the linkage (103), the recess corresponding to a first one of said grooved profiles extending more in depth in said first portion of the linkage than the recess corresponding to a second one of said grooved profiles.

15. Pump unit as claimed in claim 11, wherein said housings (105,106) are positioned at different distances from the fulcrum (107).

16. An apparatus as claimed in claim 2, wherein said pump unit comprises an elastic membrane (110) fastened to portions (101*a*,101*b*) of the chamber (101) and integrally connected to a head (102*a*) of said piston (102).

17. An apparatus as claimed in claim 3, wherein said pump unit comprises an elastic membrane (110) fastened to portions (101*a*,101*b*) of the chamber (101) and integrally connected to a head (102*a*) of said piston (102).

18. An apparatus as claimed in claim 4, wherein said pump unit comprises an elastic membrane (110) fastened to portions (101*a*,101*b*) of the chamber (101) and integrally connected to a head (102*a*) of said piston (102).

19. An apparatus as claimed in claim 5, wherein said pump unit comprises an elastic membrane (110) fastened to portions (101*a*,101*b*) of the chamber (101) and integrally connected to a head (102*a*) of said piston (102).

20. An apparatus as claimed in claim 7, wherein said elastic membrane (110) coats the head (102*a*) of the piston (102) entirely, excepting the region connecting the stem (102*b*) to the head.

* * * * *